(12) United States Patent
Kobayashi et al.

(10) Patent No.: US 7,131,976 B2
(45) Date of Patent: Nov. 7, 2006

(54) INSERTION DEVICE FOR INTRAOCULAR LENS

(75) Inventors: Kenichi Kobayashi, Tokyo (JP); Toshikazu Kikuchi, Hachioji (JP)

(73) Assignee: Canon-Staar Co. Inc., Tokyo (JP)

( * ) Notice: Subject to any disclaimer, the term of this patent is extended or adjusted under 35 U.S.C. 154(b) by 469 days.

(21) Appl. No.: 10/302,123

(22) Filed: Nov. 22, 2002

(65) Prior Publication Data
US 2003/0212409 A1   Nov. 13, 2003

(30) Foreign Application Priority Data
May 8, 2002   (JP) .............................. 2002-133182

(51) Int. Cl.
*A61F 9/00* (2006.01)
(52) U.S. Cl. .................................................. 606/107
(58) Field of Classification Search ................ 606/107, 606/181, 182, 184, 185, 167; 623/6.11, 6.12
See application file for complete search history.

(56) References Cited

U.S. PATENT DOCUMENTS

| | | | |
|---|---|---|---|
| 5,190,552 A | 3/1993 | Kelman | |
| 5,496,328 A | 3/1996 | Nakajima et al. | |
| 5,620,450 A * | 4/1997 | Eagles et al. | 606/107 |
| 6,093,193 A * | 7/2000 | Makker et al. | 606/107 |
| 6,248,120 B1 * | 6/2001 | Wyszogrodzki | 606/182 |

FOREIGN PATENT DOCUMENTS

| | | |
|---|---|---|
| JP | 58-146346 | 8/1983 |
| JP | 5-103803 | 4/1993 |
| JP | 5-103808 | 4/1993 |
| JP | 5-103809 | 4/1993 |
| JP | 7-23991 | 1/1995 |
| JP | 8-38542 | 2/1996 |

* cited by examiner

*Primary Examiner*—Kevin T. Truong
(74) *Attorney, Agent, or Firm*—Roth & Goldman, P.A.

(57) ABSTRACT

An insertion device is used to deform a deformable intraocular lens to a reduced size and insert the deformed lens into an eye through an insertion tube. The insertion device includes a push rod for pushing and inserting the lens into the eye, and a posture control member disengagably engaged with a tip end portion of the push rod. The posture control member prevents deflection of the push rod from a center axis. The engagement between the posture control member and the push rod is broken when the push rod arrives at a predetermined position during a step of advancing the push rod.

3 Claims, 7 Drawing Sheets

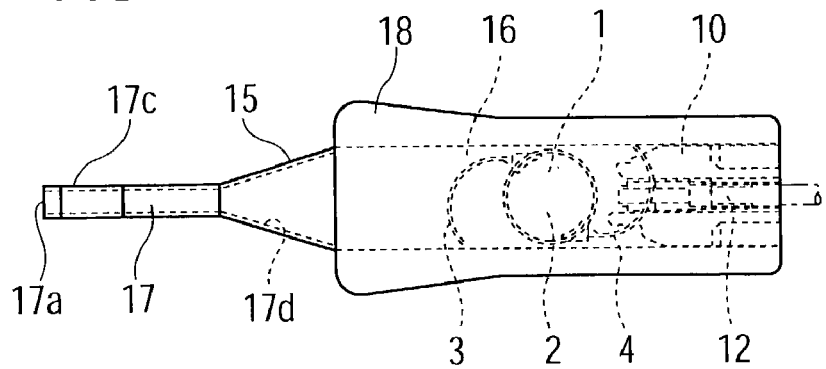
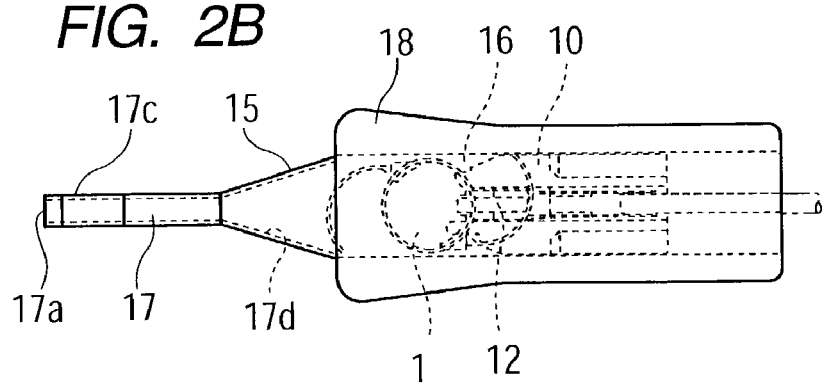
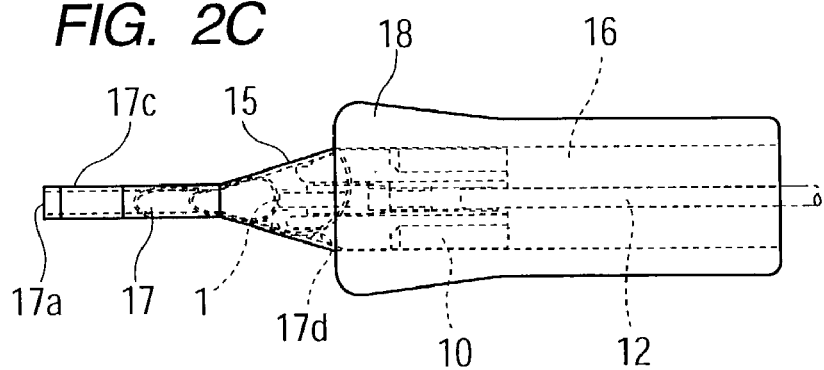
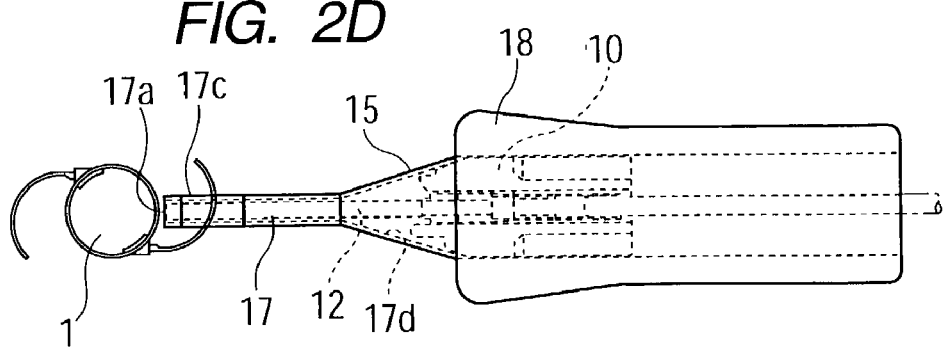

INSERTION DEVICE FOR INTRAOCULAR LENS

BACKGROUND OF THE INVENTION

1. Field of the Invention

The present invention relates to a device for inserting a deformable intraocular lens into the eye. Examples of such a deformable intraocular lens include a deformable intraocular lens that is inserted into the eye in place of the natural lens when the latter is physically extracted because of cataracts, and a vision correction lens that is inserted into the eye for the sole purpose of vision correction.

2. Description of the Related Art

In general, during cataract surgery, an intraocular lens is inserted into the eye, from which the natural lens has been removed (lens-removed eye), such that the intraocular lens is located in the original position previously occupied by the natural lens and restores vision. Various studies on the material and shape of such an intraocular lens have been carried out since Ridley performed the first implantation of an artificial lens in 1949.

In recent years, in addition to studies on intraocular lenses which are used for vision restoration after cataract surgery, intense studies on intraocular lenses for refractivity correction have been ongoing. Such an intraocular lens for refractivity correction is inserted into the eye which still has a natural lens (lens-carrying eye), for correction of nearsightedness or farsightedness.

In relation to cataract surgery, a technique for crushing the lens tissue by means of ultrasonic emulsification and suctioning the crushed tissue away has been popularized. This technique enables performance of lens removal surgery to excise an opaque lens through a small incision. Along with progress in the operational technique itself, intraocular lenses themselves have recently been improved. Such an improved intraocular lens is disclosed in, for example, Japanese Patent Application Laid-Open (kokai) No. 58-146346. In the intraocular lens, the optical portion is made of a deformable elastic material. The intraocular lens is inserted, in a folded state, into the eye through a small incision and restored to its original shape within the eye allowing it to exert its proper lens function.

Accompanying these technical developments, the material of the optical portion of such an intraocular lens has been changed gradually from hard polymethyl methacrylate (PMMA) to silicone or soft acrylic resin, which enables the intraocular lens to be inserted into the eye in a folded state.

Moreover, in recent years, studies have been conducted on copolymers such as hydroxyethyl methacrylate and methyl methacrylate, as well as on hydrophilic materials such as 2-hydroxyethyl methacrylate (HEMA).

Further, intraocular lenses of different shapes have been studied and put into practical use, including an intraocular lens having a circular optical portion and loop-shaped support portions formed of different materials, an intraocular lens whose loop-shaped support portions and optical portion are formed of the same material, and an intraocular lens having plate-shaped support portions.

Furthermore, the following patent publications disclose insertion devices for inserting the above-described deformable intraocular lens into the eye in a compressed or folded state.

(1) Japanese Patent Application Laid-Open (kokai) No. 5-103803 discloses a device designed such that a holding member which holds a folded lens is attached to a main body, and the lens is inserted into the eye through an insertion tube provided at the tip end of the holding member.

(2) Japanese Patent Application Laid-Open (kokai) No. 7-23991 discloses a disposable insertion device for one-time use in which a portion for holding a folded lens is integrated with a main body of the device and the entirety of the device is formed of resin.

The above-described are typical examples of conventional intraocular-lens insertion devices, which are divided into various types in accordance with their mechanisms for folding an lens; such as a type in which a lens is folded by use of a taper portion of a holding member, and a type in which a lens is folded by use of a hinged portion of a holding member.

However, a conventional intraocular-lens insertion device of the former type in which a lens is folded by use of a taper portion of a holding member involves the following problem. Since a space of the holding member for placement of an intraocular-lens is large, the posture of a push rod within the space cannot be controlled, and consequently the push rod deflects in the course of a step of advancing the push rod.

When the push rod deflects, the intraocular lens may be caught between the inner wall surface of the holding member and the push rod with resultant breakage of the intraocular lens, or a tip end portion of an insertion tube of the insertion device may be broken.

Meanwhile, the tip end portion of the push rod, which provides a function of pushing the intraocular lens out of the insertion device, has a diameter that is determined in accordance with the inner diameter of the insertion tube at its tip end. Therefore, in the intraocular-lens insertion device of the type in which a lens is folded by use of the taper portion (i.e., the insertion tube), the tip end of the push rod cannot be formed to have a large diameter, even though the insertion device has a large space at its lens placement section. Accordingly, when the intraocular lens is pushed out, a large load or pressure acts on the intraocular lens.

SUMMARY OF THE INVENTION

An object of the present invention is to provide an intraocular-lens insertion device which can reduce deflection of a push rod at a lens placement section of the insertion device, which deflection would otherwise arise at the time of inserting an intraocular lens as a result of a large space of the lens placement section, to thereby solve the problem involved in the conventional device.

Another object of the present invention is to provide an intraocular-lens insertion device which can push an intraocular lens within the lens placement section by use of a larger push portion, to thereby reduce the load acting on the intraocular lens.

In order to achieve the above objects, the present invention provides an insertion device for deforming a deformable intraocular lens to a reduced size and inserting the deformed lens into an eye through an insertion tube. The insertion device comprises a push rod disposed for pushing and inserting the lens into the eye, and a posture control member disengagably engaged with a tip end portion of the push rod. The posture control member prevents deflection of the push rod from a center axis. The engagement between the posture control member and the push rod is broken when the push rod arrives at a predetermined position during a step of advancing the push rod.

By virtue of the above configuration, during a step of advancing the push rod to thereby deform an intraocular lens into a smaller size, deflection of the push rod from the center axis is reduced by means of the posture control member, to thereby avoid problems which would otherwise arise in the course of insertion of the intraocular lens. Further, the engagement between the posture control member and the push rod is broken when the push rod arrives at a predetermined position in the course of a step of advancing the push rod; for example, when the posture control member comes into contact with a tapered inner wall surface of a taper portion of the lens placement section. This enables the push rod to pass through the insertion tube, irrespective of presence of the posture control member, which is larger than the interior space of the insertion tube.

Preferably, the posture control member has an asymmetrical shape with respect to the center axis. Since the intraocular lens typically has an asymmetrical shape with respect to the center axis, the asymmetrical shape of the posture control member increases the area of contact between the posture control member and the intraocular lens, to thereby enable smooth deformation of the intraocular lens into a smaller size.

Preferably, a tip end portion of the posture control member assumes a shape capable of pushing the intraocular lens forward. In this case, during a first half of the insertion step, the intraocular lens can be pushed forward by means of the posture control member, which has a wider pushing area than does the push rod. Thus, the load or pressure acting on the intraocular lens can be reduced.

Preferably, the posture control member assumes a shape so as to push the intraocular lens forward in cooperation with the push rod. In this case, at the lens placement section having a large space, the intraocular lens can be pushed forward by the tip ends of a plurality of members; i.e., the posture control member and the push rod, whereby the number of points of contact with the intraocular lens increases, thereby reducing the load or pressure acting on the intraocular lens. Moreover, since the intraocular lens can be pushed evenly by the tip ends of a plurality of members, a change in posture, such as rotation, of the intraocular lens can be controlled, to thereby avoid problems which would otherwise arise in the course of insertion of the intraocular lens.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which:

FIGS. 2A to 2D are enlarged plan views, each showing the positional relation among an intraocular lens, a holding member, a push rod, and a posture control member of the insertion device, wherein FIG. 2A shows a state at the beginning of an insertion step, FIG. 2B shows a state in which the push rod and the posture control member, while connected with each other, are advanced so as to push the intraocular lens forward, FIG. 2C shows a state in which the engagement between the push rod and the posture control member has been cancelled, and the intraocular lens is pushed forward by sole use of the push rod, and FIG. 2D shows a state in which the intraocular lens has been pushed out the tip end of the insertion tube;

FIGS. 3A to 3C are enlarged cross sectional views of a main potion of the insertion device, wherein FIG. 3A shows a sate in which the engagement between the push rod and the posture control member has been established through engagement between a groove and a projection formed on these members, FIG. 3B relates to an alternative manner of establishing engagement between the push rod and the posture control member and shows an initial state before establishment of the connection, and FIG. 3C relates to the alternative manner and shows a state in which the connection has been established;

FIGS. 5A and 5B are cross sectional views, wherein FIG. 5A shows the positional relation among the holding member, the push rod, and the posture control member in the insertion device according to the present invention, and FIG. 5B shows the positional relation between the holding member and the push rod in a conventional insertion device;

FIGS. 8A and 8B are views showing a modified example of the insertion tube of the insertion device of the present invention, wherein FIG. 8A is a plan view of the insertion tube, and FIG. 8B is a cross sectional view taken along line 8B—8B in FIG. 8A.

DETAILED DESCRIPTION OF PREFERRED EMBODIMENT

An embodiment of the present invention will be described with reference to the drawings.

Figure 1:
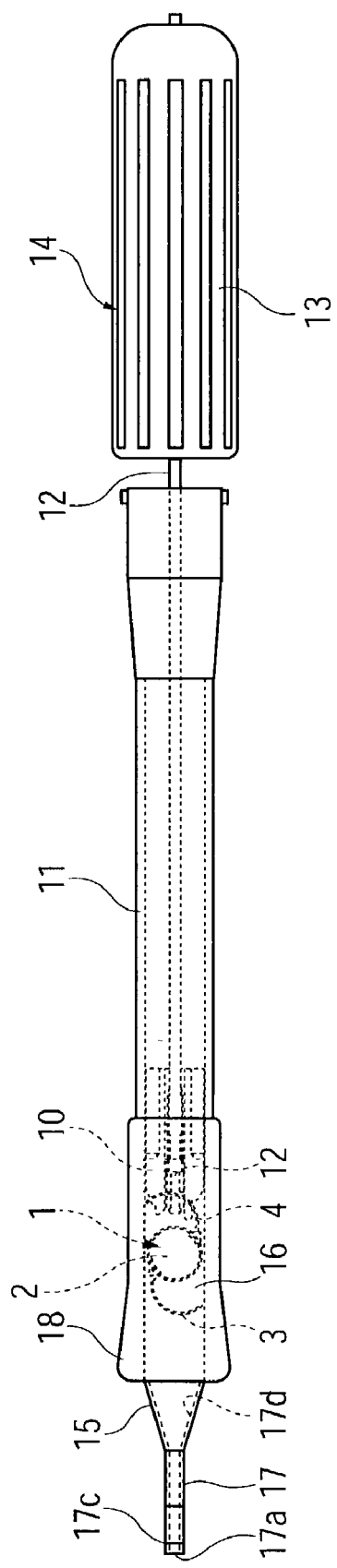
FIG. 1 is a plan view of an intraocular-lens insertion device according to an embodiment of the present invention.

FIG. 1 is a plan view of an intraocular-lens insertion device according to the present invention.

The insertion device is mainly composed of a generally tubular main body 11, a pusher mechanism 14, and a holding member 18. The pusher mechanism 14 includes a push rod 12 inserted into the main body 11, and a threaded sleeve 13 to be screw-engaged with a rear end of the main body 11. The holding member 18 includes a lens placement section 16, which, instead of having a hinge portion, includes a taper portion 15 for deforming an intraocular lens 1 into a smaller size; and an insertion tube 17, which projects from the tip end of the taper portion 15. The holding member 18 is fixedly attached to the tip end of the main body 11. Specifically, a depressed portion and a projecting portion are formed on the tip end of the main body 11 and the rear end of the holding member 18, respectively; and the holding member 18 is attached to the main body 11 through engagement between the depressed portion and the projecting portion. A posture control member 10 for preventing deflection of the push rod 12 is axially movably disposed in the holding member 18 at an axial position corresponding to the tip end portion of the push rod 12. The posture control member 10 assumes a shape for enabling engagement with the push rod 12 for movement therewith. The push rod 12 is rotatably connected to the threaded sleeve 13, but is prevented from rotating relative to the main body 11.

FIGS. 2A to 2D are enlarged plan views of the holding member 18 of the insertion device, each showing the positional relation among the intraocular lens 1, the holding member 18, the push rod 12, and the posture control member 10. Specifically, FIG. 2A shows a state before the push rod 12 is advanced; and FIG. 2B shows a state in which the intraocular lens 1 is pushed forward by means of the push rod 12 and the posture control member 10, which is engaged with the push rod 12 for unitary movement therewith. FIG. 2C shows a state in which, as a result of advancement of the push rod 12, the intraocular lens 1 is deformed into a smaller size by means of the taper portion 15, and the engagement between the push rod 12 and the posture control member 10 is broken as a result of engagement between the posture control member 10 and the inner wall surface of the taper portion 15. FIG. 2D shows a state in which the intraocular lens 1 is ejected from a slit 17c formed in a tip end portion 17a of the insertion tube 17 by means of the push rod 12.

Figure 3A:
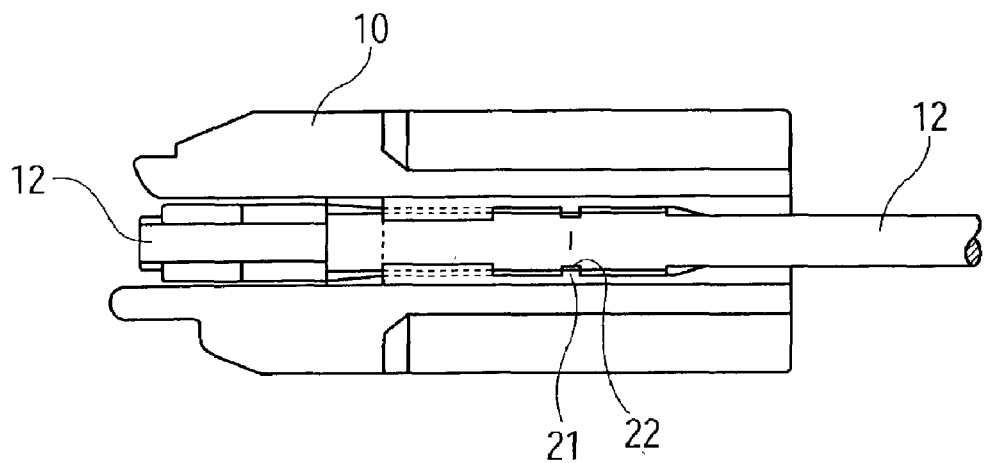

FIG. 3A shows the engagement between the push rod 12 and the posture control member 10. A projection 21 formed on the posture control member 10 is fitted into a groove 22 formed on the push rod 12. Since the push rod 12 and the posture control member 10 are both formed of an elastic material such as a synthetic resin, the engagement between the projection 21 and the groove 22 is broken when the advance movement of the push rod 12 is continued after abutment of the posture control member 10 against the inner wall surface of the taper portion 15.

Figure 3B:
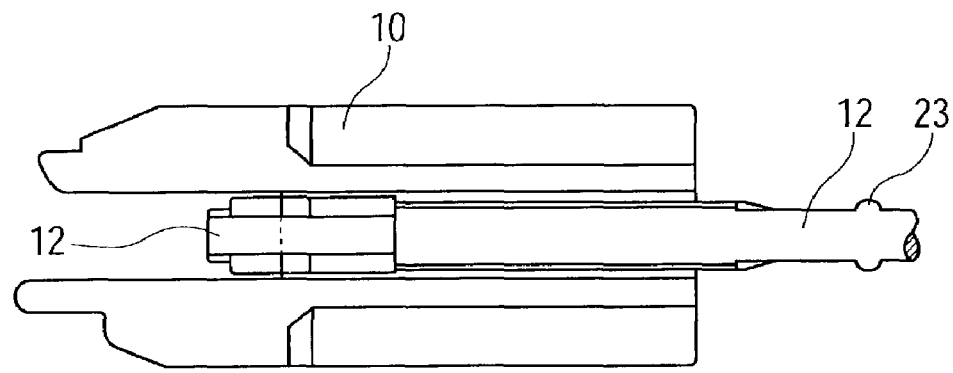
Figure 3C:
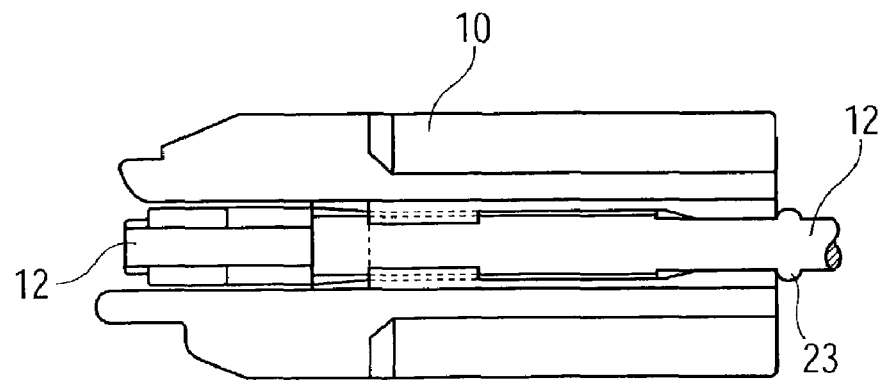

FIGS. 3B and 3C show an alternative manner of establishing engagement between the push rod 12 and the posture control member 10. In this case, an annular projection 23 is integrally formed on the outer circumference of the push rod 12. The annular projection 23 has an outer diameter slightly greater than the diameter of the center hole of the posture control member 10. In the initial state shown in FIG. 3B, the projection 23 is separated from the posture control member 10, so that the push rod 12 moves independently of the posture control member 10. When the annular projection 23 comes into engagement with the posture control member 10 as shown in FIG. 3C, the posture control member 10 moves together with the push rod 12, to thereby start unitary movement of the posture control member 10 and the push rod 12. Since the push rod 12; i.e., the projection 23, is formed of an elastic material such as a synthetic resin, when the movement of the posture control member 10 is stopped, the projection 23; i.e., the push rod 12, moves relative to the posture control member 10.

Therefore, in both the structure shown in FIG. 3A and the structure shown in FIGS. 3B and 3C, when the posture control member 10 abuts against a projection or the inner wall surface of the taper portion 15, the advance movement of the posture control member 10 is stopped, so that engagement between the posture control member 10 and the push rod 12 is broken. As a result, only the push rod 12 is advanced so as to advance the intraocular lens 1.

Figure 4:
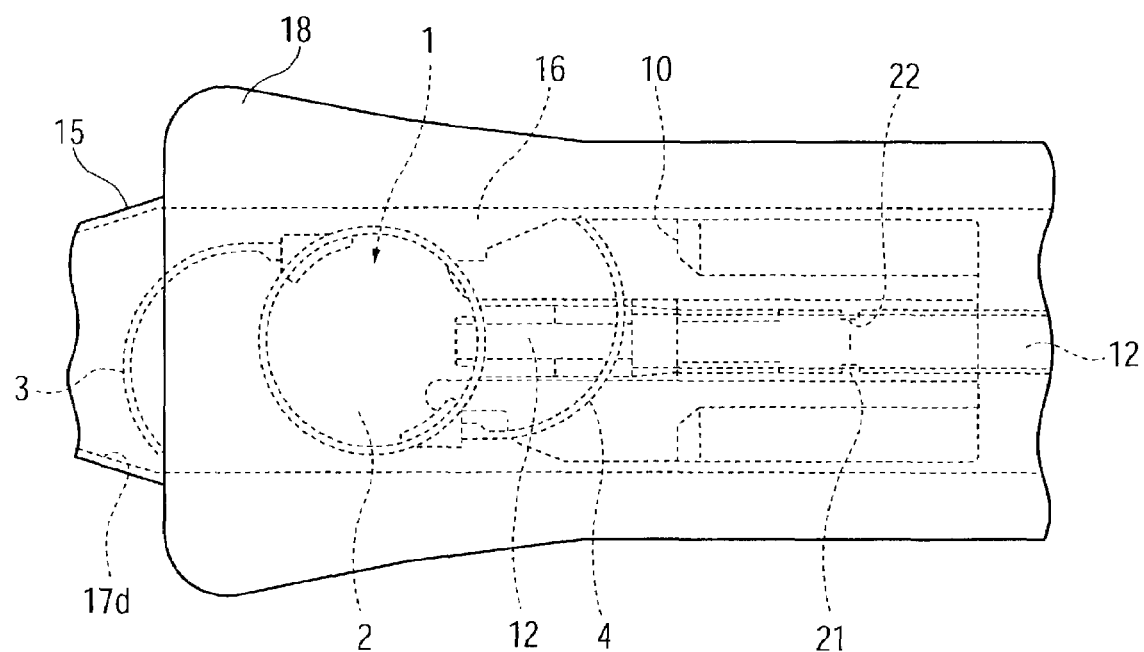
FIG. 4 is an enlarged plan view of a main portion of the insertion device showing that the posture control member has an asymmetrical shape with respect to the longitudinal center or center axis of the insertion device.

FIG. 4 sows a state in which the push rod 12 and the posture control member 10 cooperate to advance the intraocular lens 1 within the lens placement section 16. In general, the intraocular lens 1 includes an optical portion 2 and support portions 3 and 4 and assumes an asymmetric shape. Further, the support portions 3 and 4 extend from the optical portion 2 while forming acute angles with respect to the periphery of the optical portion 2. Therefore, when viewed from above, the tip end portion of the posture control member 10 has an asymmetric shape with respect to the center axis, which extends along the longitudinal direction. This asymmetric shape improves the degree of engagement between the intraocular lens 1 and the posture control member 10, to thereby enable smooth pushing and deformation of the intraocular lens 1. However, needless to say, no functional problem arises even when the tip end portion of the posture control member 10 assumes a symmetric shape.

Figure 5A:
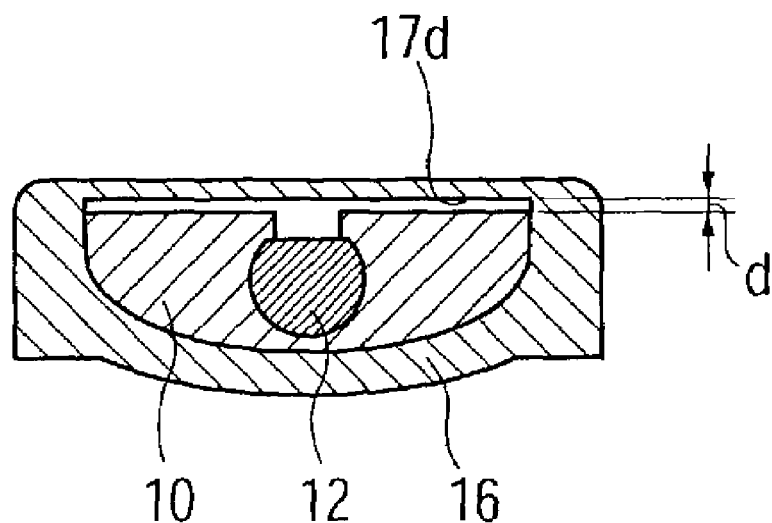

FIG. 5A is a sectional view showing the positional relation between the push rod 12 and the posture control member 10 at the lens placement section 16. As is apparent from FIG. 5A, a small clearance is provided between the top surface of the posture control member 10 and the inner wall surface 17d of the lens placement section 16. Since the size d of the clearance d is determined so as to accommodate the support portions 3 and 4 of the intraocular lens 1 in the clearance, the support portions 3 and 4 are prevented from being caught between the top surface of the posture control member 10 and the inner wall surface 17d of the lens placement section 16.

Figure 5B:
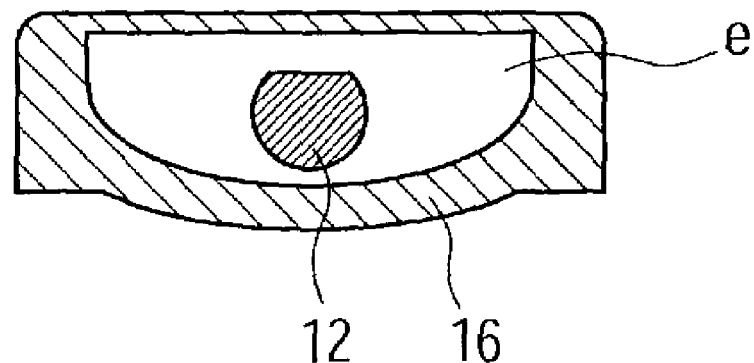

FIG. 5B is a sectional view showing the positional relation between the push rod 12 and the lens placement section 16 of a conventional insertion device, for comparison with that in the present invention. Since a large space e is formed between the push rod 12 and the lens placement section 16, the push rod 12 is apt to deviate from its original position; i.e., the center axis. Further, the large space e uselessly consumes a large amount of a hyaluronic-acid-containing agent serving as a lubricant. Specifically, since the push rod 12 is thin, even after the intraocular lens 1 is inserted into the eye by means of the push rod 12, a large portion of the hyaluronic-acid-containing agent injected or applied to the large space e remains within the space.

Figure 6A:
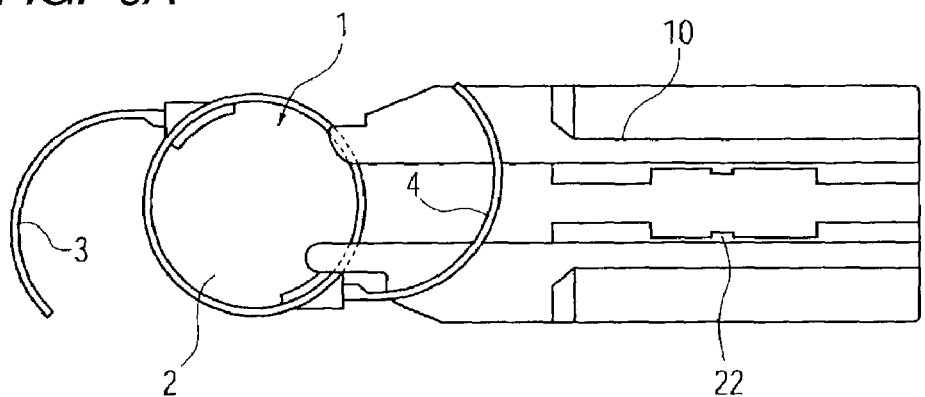
FIGS. 6A and 6B are plan and side views of the posture control member used in the insertion device of the present invention, showing a state in which an intraocular lens is pushed forward by the posture control member.
Figure 6B:
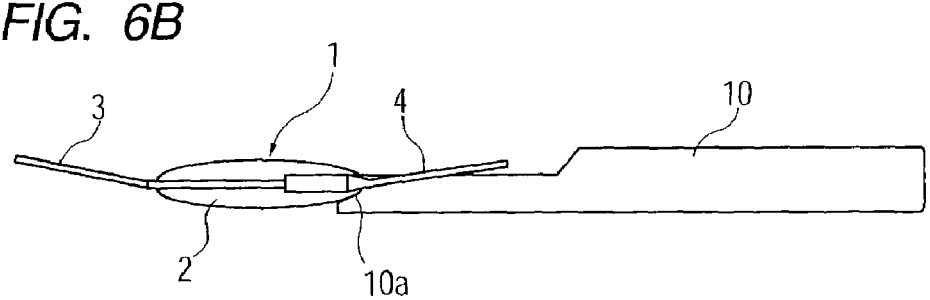

FIGS. 6A and 6B are enlarged views showing a state in which the intraocular lens 1 is pushed forward by means of the posture control member 10.

A cut having a V-like shape is formed at the tip end portion 10a of the posture control member 10 in order to facilitate the pushing of the intraocular lens 1. Notably, the intraocular lens 1 can be pushed forward by means of the posture control member 10 even when the tip end portion 10a of the posture control member 10 does not has a V-shaped cut, so long as the tip end portion 10a of the posture control member 10 has a shape that enables interference with the intraocular lens 1.

Figure 7A:
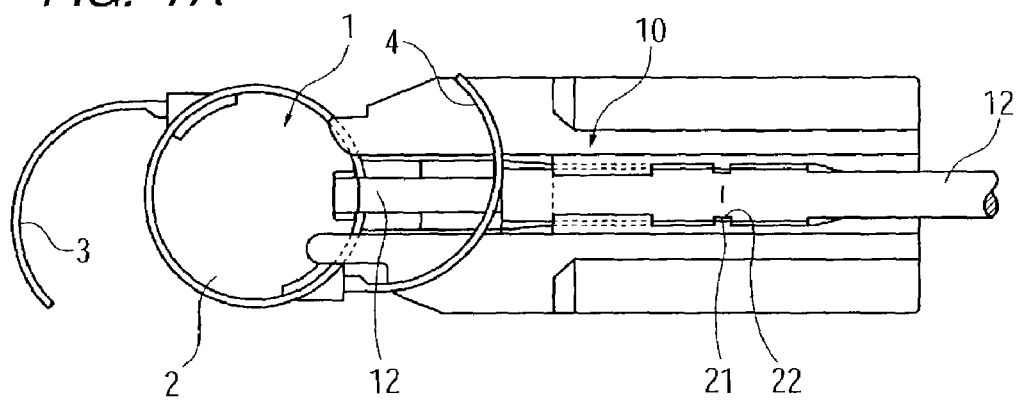
FIGS. 7A and 7B are plan and side views of the posture control member used in the insertion device of the present invention, showing a state in which an intraocular lens is pushed forward by the posture control member and the push rod.
Figure 7B:
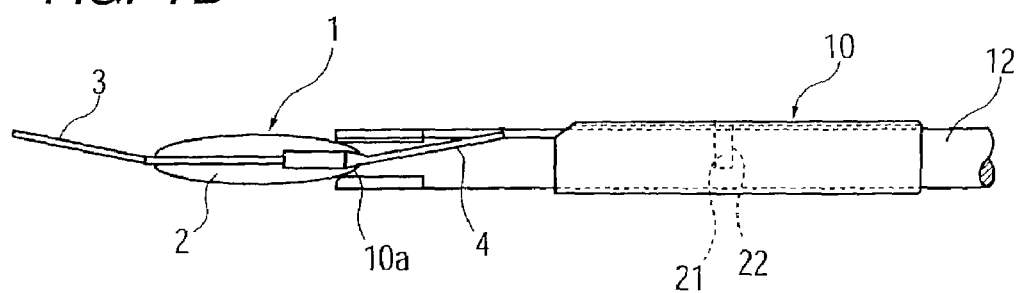

FIGS. 7A and 7B are enlarged views showing a state in which the intraocular lens 1 is pushed forward by means of the posture control member 10 and the push rod 12.

Since the posture control member 10 and the push rod 12 come into contact with the intraocular lens 1 at a plurality of locations, rotation of the intraocular lens 1 during the course of its advancement is prevented. Further, when the tip end portion 10a of the posture control member 10 has a V-shaped cut, the rotation of the intraocular lens 1 can be prevented more reliably.

Figure 8A:
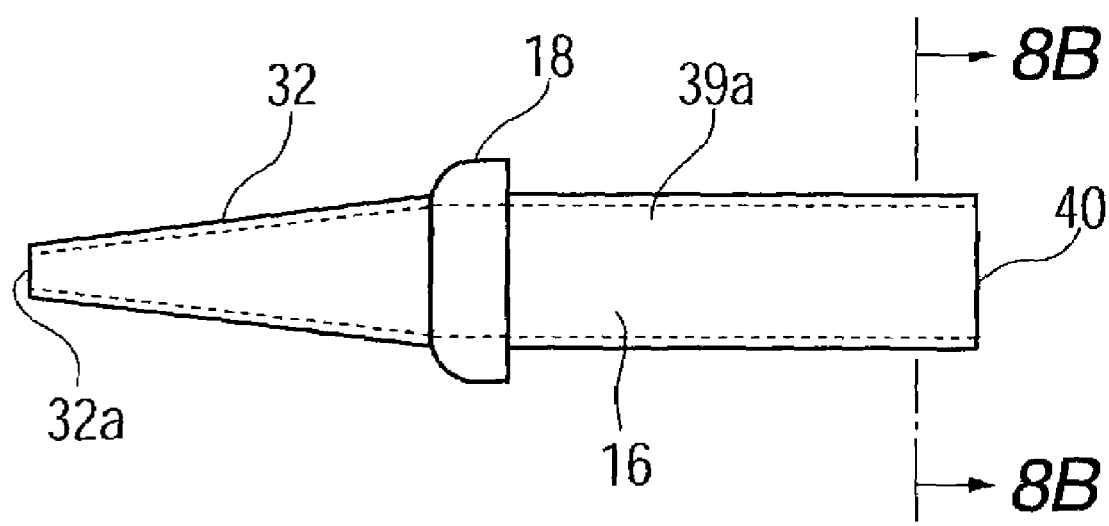
Figure 8B:
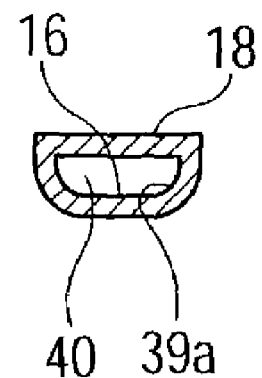

FIGS. 8A and 8B are views showing a modified example of the insertion tube of the insertion device of the present invention.

In FIGS. 8A and 8B, reference numeral 18 denotes a tubular lens holding member. A tapered insertion tube 32 extends from the tip end of the lens holding member 18; and the tip end portion of the insertion tube 32 has an opening 32a. Reference numeral 16 denotes a lens placement section; and its inside chamber has a curved inner wall surface 39a. An intraocular lens 1 is inserted into the inside chamber through a lens insertion section 40 provided at the rear end of the lens placement section 16. Subsequently, the lens holding member 18 is fixedly attached to the main body 11. Since the structure of the remaining portion is the same as that of the above-described embodiment, repeated description thereof is omitted. In the structure shown in FIGS. 8A and 8B, the intraocular lens 1 is deformed into a reduced size by means of the tapered insertion tube 32. The present invention can be applied to insertion devices having such a structure.

Obviously, numerous modifications and variations of the present invention are possible in light of the above teachings. It is therefore to be understood that within the scope of the appended claims, the present invention may be practiced otherwise than as specifically described herein.

What is claimed is:

1. An insertion device for deforming a deformable intraoccular lens to a reduced size and inserting the deformed lens into an eye through an insertion tube, comprising:

a push rod having a lens engagement tip configured for pushing and inserting the lens into the eye; and a posture control member guiding said push rod to prevent deflection of the push rod from a center axis, said posture control member including a tip end configured for pushing the intraoccular lens forward, said push rod and said posture control member being connected for movement longitudinally together until the posture control member is prevented from further movement by engagement with a portion of the insertion device, said push rod thereafter continuing to move independently of said posture control member.

2. An insertion device according to claim 1, wherein the posture control member has an asymmetrical shape with respect to the center axis.

3. An insertion device according to claim 1, wherein said lens engagement tip of said push rod and said tip end of said posture control member simultaneously engage and push said intraocular lens forward.

* * * * *